(12) United States Patent
Zhang et al.

(10) Patent No.: US 8,135,471 B2
(45) Date of Patent: Mar. 13, 2012

(54) METHOD AND APPARATUS FOR INSPIRATORY MUSCLE STIMULATION USING IMPLANTABLE DEVICE

(75) Inventors: Yi Zhang, Blaine, MN (US); Shantha Arcot-Krishnamurthy, Roseville, MN (US); Lili Liu, Maple Grove, MN (US); Kenneth C. Beck, St. Paul, MN (US); Kent Lee, Shoreview, MN (US); Jonathan Kwok, Denville, NJ (US); Zheng Lin, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 161 days.

(21) Appl. No.: 11/895,999

(22) Filed: Aug. 28, 2007

(65) Prior Publication Data

US 2009/0062882 A1     Mar. 5, 2009

(51) Int. Cl.
   *A61N 1/36*      (2006.01)
(52) U.S. Cl. .............. 607/42; 600/529; 607/2; 607/116
(58) Field of Classification Search .................. 600/529; 607/2, 42, 116, 118, 126
   See application file for complete search history.

(56) References Cited

U.S. PATENT DOCUMENTS

| 4,135,518 | A | * | 1/1979 | Dutcher ......................... 600/374 |
| 6,132,384 | A | * | 10/2000 | Christopherson et al. .... 600/529 |
| 6,141,594 | A | | 10/2000 | Flynn et al. |
| 6,415,183 | B1 | | 7/2002 | Scheiner et al. |
| 6,463,334 | B1 | | 10/2002 | Flynn et al. |
| 6,915,169 | B2 | | 7/2005 | Flynn et al. |
| 7,277,761 | B2 | | 10/2007 | Shelchuk |
| 7,421,296 | B1 | | 9/2008 | Benser et al. |
| 7,430,447 | B2 | | 9/2008 | Min et al. |
| 2004/0088015 | A1 | | 5/2004 | Casavant et al. |
| 2004/0111040 | A1 | * | 6/2004 | Ni et al. ......................... 600/534 |
| 2004/0243210 | A1 | * | 12/2004 | Morgan et al. ................ 607/122 |
| 2005/0085734 | A1 | | 4/2005 | Tehrani |
| 2005/0085865 | A1 | | 4/2005 | Tehrani |
| 2005/0085866 | A1 | | 4/2005 | Tehrani |
| 2005/0085867 | A1 | | 4/2005 | Tehrani et al. |
| 2005/0085868 | A1 | | 4/2005 | Tehrani et al. |
| 2005/0085869 | A1 | | 4/2005 | Tehrani et al. |
| 2005/0107838 | A1 | | 5/2005 | Lovett et al. |
| 2005/0165457 | A1 | | 7/2005 | Benser et al. |
| 2006/0030894 | A1 | | 2/2006 | Tehrani |
| 2006/0036294 | A1 | | 2/2006 | Tehrani |

(Continued)

FOREIGN PATENT DOCUMENTS

DE     112004001957     8/2006

(Continued)

OTHER PUBLICATIONS

"Application Serial No. PCT/US2008/009725, International Search Report mailed Oct. 29, 2008", 4 pgs.

(Continued)

*Primary Examiner* — Carl H Layno
*Assistant Examiner* — Jennifer Stewart
(74) *Attorney, Agent, or Firm* — Schwegman, Lundberg & Woessner, P.A.

(57) ABSTRACT

An inspiratory muscle stimulation system uses an implantable medical device to deliver stimulation to control diaphragmatic contractions for slower and deeper breathing, thereby conditioning and strengthening inspiratory muscles. In various embodiments, respiratory and/or cardiac performance are monitored for controlling parameters of the stimulation.

21 Claims, 8 Drawing Sheets

U.S. PATENT DOCUMENTS

| | | | |
|---|---|---|---|
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0247729 A1 | 11/2006 | Tehrani et al. | |
| 2007/0118183 A1 | 5/2007 | Gelfand et al. | |
| 2007/0156199 A1* | 7/2007 | Koh et al. | 607/42 |
| 2008/0021504 A1 | 1/2008 | McCabe et al. | |
| 2008/0183187 A1* | 7/2008 | Bly | 606/129 |
| 2008/0183254 A1* | 7/2008 | Bly et al. | 607/116 |
| 2008/0188904 A1 | 8/2008 | Tehrani et al. | |

FOREIGN PATENT DOCUMENTS

| | | |
|---|---|---|
| WO | WO-2005037077 | 4/2005 |
| WO | WO-2005037172 | 4/2005 |
| WO | WO-2005037173 | 4/2005 |
| WO | WO-2005037174 | 4/2005 |
| WO | WO-2005037220 | 4/2005 |
| WO | WO-2005037366 | 4/2005 |
| WO | WO-2007/058938 A2 | 5/2007 |
| WO | WO-2007058938 | 5/2007 |
| WO | WO-2009/029172 A1 | 3/2009 |

OTHER PUBLICATIONS

"Application Serial No. PCT/US2008/009725, Written Opinion mailed Oct. 29, 2008", 7 pgs.

Bernardi, L., et al., "Slow breathing increases arterial baroreflex sensitivity in patients with chronic heart failure", *Circulation*, 105(2), (2002),143-5.

Dall'ago, P., et al., "Inspiratory muscle training in patients with heart failure and inspiratory muscle weakness: a randomized trial.", *J Am Coll Cardiol.*, 47(4), (2006),757-63.

Glenn, W. W., et al., "Ventilatory support by pacing of the conditioned diaphragm in quadriplegia", *N. Engl J Med.*, 310(18), (1984),1150-5.

Ishii, K., et al., "Effects of bilateral transvenous diaphragm pacing on hemodynamic function in patients after cardiac operations. Experimental and clinical study", *J Thorac Cardiovasc Surg.*, Jul.;100 1:, (1990), 108-14.

Mancini, D. M., et al., "Benefit of selective respiratory muscle training on exercise capacity in patients with chronic congestive heart failure.", *Circulation*, 91(2), (1995),320-9.

Meyer, F. J., et al., "Respiratory muscle dysfunction in congestive heart failure: clinical correlation and prognostic significance.", *Circulation*, 103(17), (2001),2153-8.

Mier, A., et al., "Phrenic nerve stimulation in normal subjects and in patients with diaphragmatic weakness", *Thorax*, 42(11), (1987),885-8.

Nanas, S., et al., "Respiratory muscles performance is related to oxygen kinetics during maximal exercise and early recovery in patients with congestive heart failure.", *Circulation*, 100(5), (1999),503-8.

Series, F., et al., "Inspiratory flow dynamics during phrenic nerve stimulation in awake normals during nasal breathing.", *Am J Respir Crit Care Med.*, 160(2), (1999),614-20.

Vaseghi, M., et al., "Beyond coronary sinus angiography: the value of coronary arteriography and identification of the pericardiophrenic vein during left ventricular lead placement", *Pacing Clin Electrophysiol.*, 28(3), (2005),185-90.

Wilcox, P. G., et al., "Conditioning of the diaphragm by phrenic nerve pacing in primary alveolar hypoventilation", *Thorax*, 43(12), (1988),1017-8.

"Australian Application Serial No. 2008293985, Request to Amend filed Dec. 7, 2011", (including First Statement of Proposed Amendments), 24 pgs.

* cited by examiner

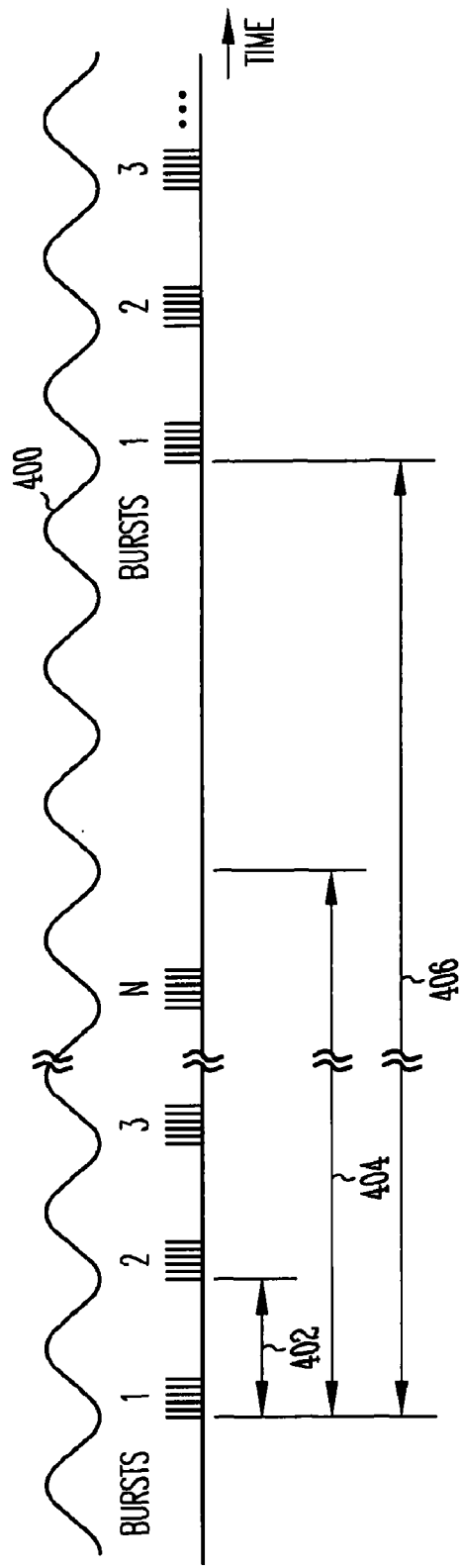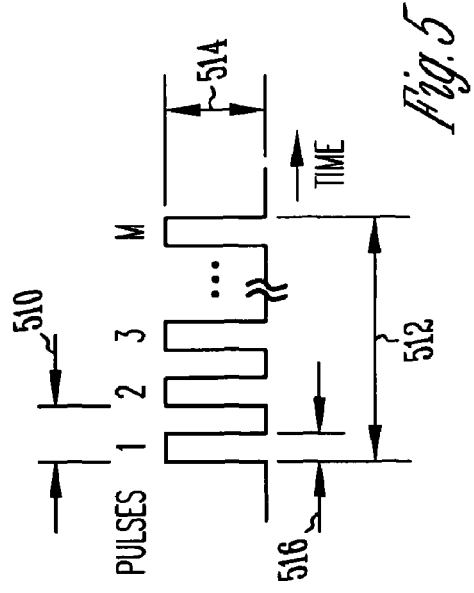

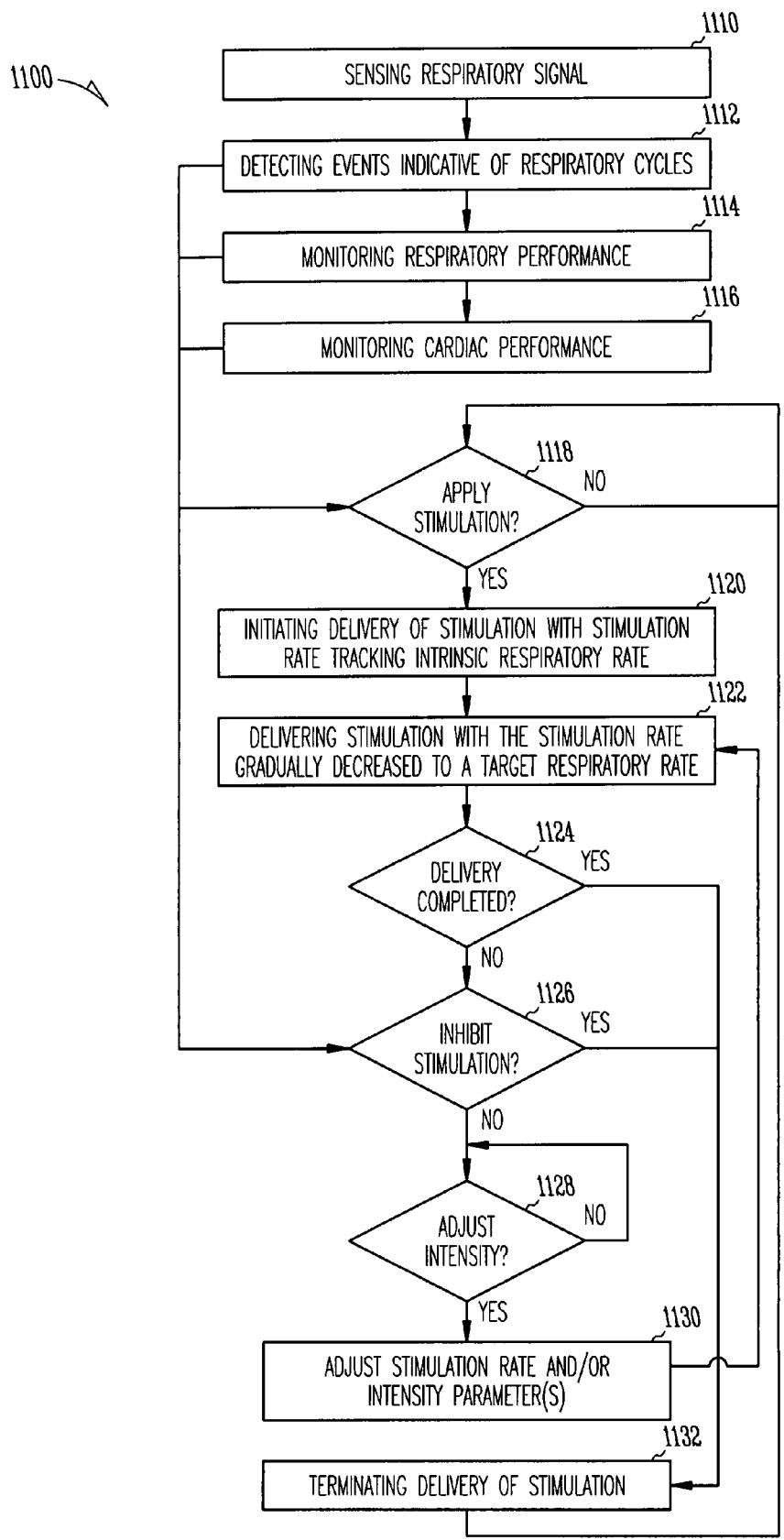

METHOD AND APPARATUS FOR INSPIRATORY MUSCLE STIMULATION USING IMPLANTABLE DEVICE

TECHNICAL FIELD

This document relates generally to medical devices and particularly to an implantable system providing for stimulation of inspiratory muscles.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs from functioning properly and causing various symptoms.

Impaired respiratory performance is among the various symptoms commonly associated with heart failure, which is a cause of inspiratory muscle weakness. Strength of the inspiratory muscle is known as an independent predictor of prognosis in heart failure. A heart failure patient may suffer from breathing disturbances due to the inspiratory muscle weakness. For these and other reasons, there is a need for improving respiratory performance in heart failure patients.

SUMMARY

An inspiratory muscle stimulation system uses an implantable medical device to deliver stimulation to control diaphragmatic contractions for slower and deeper breathing, thereby conditioning and strengthening inspiratory muscles. In various embodiments, respiratory and/or cardiac performance are monitored for controlling parameters of the stimulation.

In one embodiment, an implantable medical device includes a respiratory sensor, a respiratory cycle detector, a stimulation circuit, and a stimulation controller. The respiratory sensor senses a respiratory signal. The respiratory cycle detector detects events indicative of respiratory cycles using the respiratory signal. The respiratory cycles are indicative of an intrinsic respiratory rate. The stimulation circuit delivers stimulation. The stimulation controller controls the delivery of the stimulation and includes a stimulation rate adjuster. The stimulation rate adjuster causes the stimulation to be delivered at a stimulation rate that is approximately equal to the intrinsic respiratory rate, and then decreases the stimulation rate at a rate allowing the respiratory cycles to adapt to the stimulation rate until the stimulation rate reaches a specified target respiratory rate.

In one embodiment, an implantable transvenous lead is provided for use with the implantable medical device to deliver stimulation to one of left and right phrenic nerves via one of left and right pericardiophrenic veins. The lead includes a proximal end, a distal end, an elongate body between the proximal end and the distal end, one or more stimulation electrodes, and a gravity fixation device. The proximal end is to be connected to the implantable medical device. The distal end is to be placed in one of the left and right pericardiophrenic veins. The one or more stimulation electrodes are distributed on one or more of the distal end and the elongate body to deliver stimulation to the one of the left and right phrenic nerves. The gravity fixation device is at the distal end and has a weight suitable for substantially stabilizing the distal end in the one of the left and right pericardiophrenic veins.

In one embodiment, a method for respiratory control using an implantable medical device is provided. A respiratory signal is sensed. Events indicative of respiratory cycles are detected using the respiratory signal. The respiratory cycles are indicative of an intrinsic respiratory rate. A delivery of stimulation at a stimulation rate approximately equal to the intrinsic respiratory rate is initiated. The delivery of the stimulation is synchronized to the respiratory cycles. The stimulation rate is decreased at a rate that allows the respiratory cycles to adapt to the stimulation rate until the stimulation rate reaches a target respiratory rate.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 4 is a timing diagram illustrating an embodiment of stimulation parameters for inspiratory muscle stimulation.

FIG. 5 is an illustration of an embodiment of a burst of electrical pulses for inspiratory muscle stimulation.

FIG. 11 is a flow chart illustrating another embodiment of a method for inspiratory muscle stimulation.

DETAILED DESCRIPTION

Figure 1:
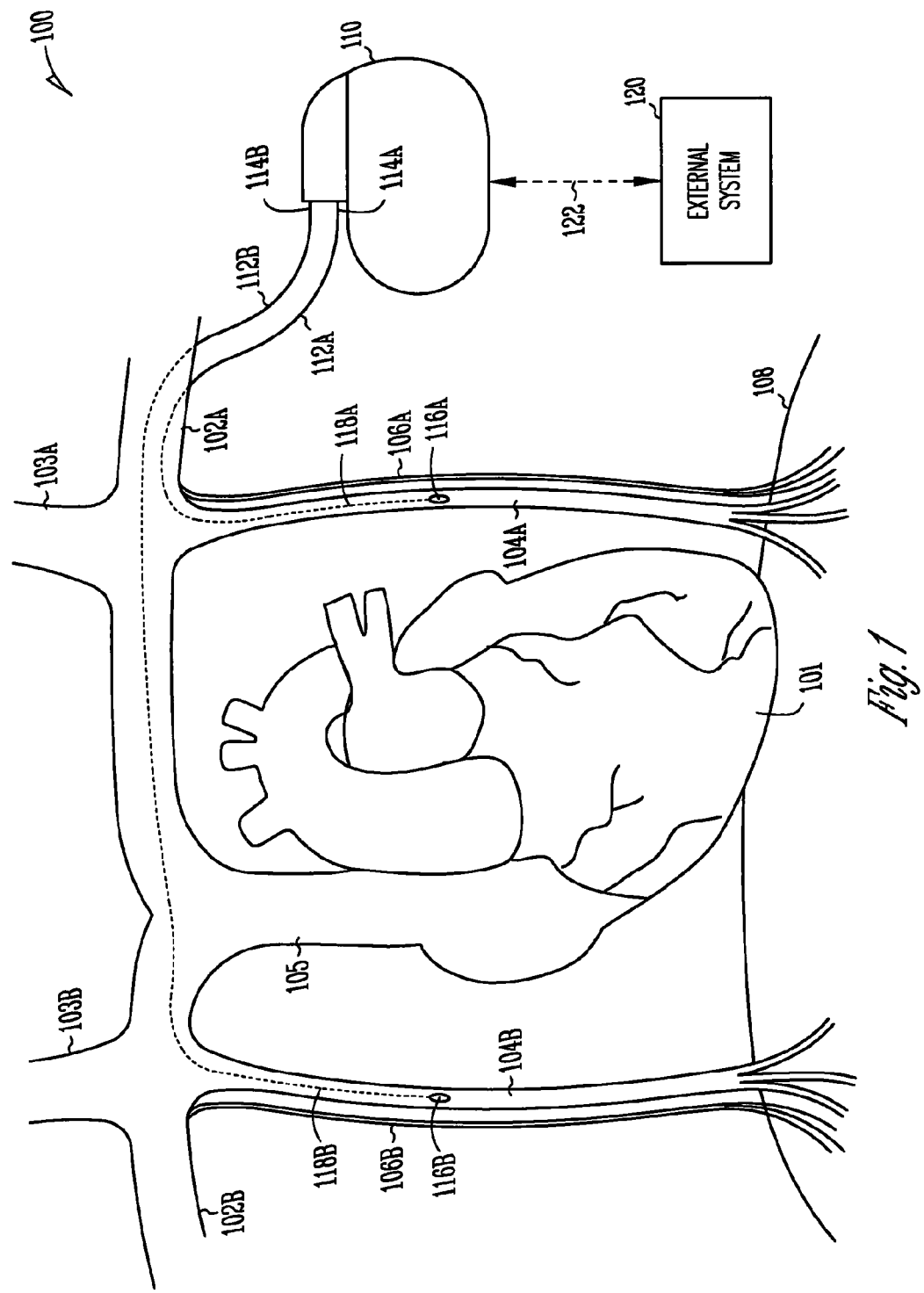
FIG. 1 is an illustration of an embodiment of an inspiratory muscle stimulation system and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses inspiratory muscle stimulation using an implantable system. An implantable medical device delivers stimulation that controls diaphragmatic contractions in a manner that promotes deeper, slower breathing, as indicated by increased tidal volume while maintaining minute ventilation in a specified range. In various embodiments, the inspiratory muscle stimulation is applied to (1) enhance respiratory capacity of a heart failure patient by conditioning and strengthening the inspiratory muscle, (2) regulate autonomic balance between sympathetic and parasympathetic tones, (3) improve respiratory performance by treating breathing disorders such as central sleep apnea syndromes, congenital central hypoventilation syndrome, and respiratory disorders resulting from high spinal cord injury or brain stem injury, and (4) improve cardiac performance such as regulating blood pressure and increasing blood return and cardiac output. In one embodiment, the stimulation is delivered by tracking the patient's intrinsic respiratory cycles to entrain the patient's breathing. After the patient's respiratory cycle is under control of the stimulation, the stimulation rate is gradually reduced in a manner that allows the patient's respiratory cycle to adapt to the stimulation rate. In one embodiment, the stimulation rate is adjusted while maintaining the minute ventilation at a substantially constant value or within a specified range. In one embodiment, the stimulation is delivered bilaterally using implantable transvenous leads with electrodes placed in left and right pericardiophrenic veins adjacent to the left and right phrenic nerves. The stimulation causes balanced diaphragmatic contractions by activating both the left and right phrenic nerves. In various embodiments, respiratory performance and/or cardiac performance are monitored for starting a delivery of the stimulation, stopping the delivery of the stimulation, and/or adjusting stimulation parameters.

In this document, unless noted otherwise, "the stimulation" refers to inspiratory muscle stimulation for controlling diaphragmatic contractions. The relationship between a respiratory rate (also known as breathing rate) and a respiratory cycle length (also known as breathing interval), as used in this document, is the relationship between a frequency and its corresponding period. If a respiratory rate is given in breaths per minute, its corresponding respiratory cycle length in seconds is calculated by dividing 60 by the respiratory rate (where 60 is the number of seconds in a minute). Any process, such as a comparison, using a respiratory rate is to be modified accordingly when a respiratory cycle length is used instead. For example, if a low respiratory rate is detected when the respiratory rate falls below a threshold rate, an equivalent process is to detect the low respiratory rate when the respiratory cycle length exceeds a corresponding threshold interval. Similarly, the relationship between a stimulation rate and a stimulation interval, as used in this document, is the relationship between a frequency and its corresponding period. If a stimulation rate is given in stimuli per minute, its corresponding interval in seconds is calculated by dividing 60 by the stimulation rate (where 60 is the number of seconds in a minute). This applies to other stimulation parameters that can be expressed as a rate (frequency) or an interval (period). The appended claims should be construed to cover such variations.

FIG. 1 is an illustration of an embodiment of an inspiratory muscle stimulation system 100 and portions of an environment in which system 100 is used. System 100 includes an implantable medical device 110, implantable transvenous leads 112A-B, an external system 120, and a telemetry link 122 providing for communication between implantable medical device 110 and external system 120.

System 100 controls contractions of a diaphragm 108 using artificial stimulation. FIG. 1 illustrates portions of a left subclavian vein 102A, a right subclavian vein 102B, a left internal jugular vein 103A, a right internal jugular vein 103B, a left pericardiophrenic vein 104A, a right pericardiophrenic vein 104B, a superior vena cava 105 connected to a heart 101, a left phrenic nerve 106A, a right phrenic nerve 106B, and diaphragm 108. Left and right phrenic nerves 106A-B supply diaphragm 108 with neural signals that activate diaphragm 108 to cause the diaphragmatic contractions and hence breathing. Left pericardiophrenic vein 104A and left phrenic nerve 106A are adjacent to each other. Right pericardiophrenic vein 104B and right phrenic nerve 106B are adjacent to each other. In the illustrated embodiment, system 100 controls contractions of diaphragm 108 by delivering the stimulation to left and right phrenic nerves 106A-B through electrodes placed in left and right pericardiophrenic veins 104A-B.

Implantable medical device 110 delivers the stimulation and controls the delivery of the stimulation using stimulation parameters. In various embodiments, implantable medical device 110 monitors respiratory performance and/or cardiac performance to start a delivery of the stimulation, stop the delivery of the stimulation, and adjust the stimulation parameters based on the patient's needs, effects of the stimulation, and safety considerations. In various embodiments, in addition to the inspiratory muscle stimulation, implantable medical device 110 includes other therapeutic and/or monitoring functions. Examples of such therapeutic functions include cardiac pacing, cardioversion/defibrillation, cardiac resynchronization therapy (CRT), cardiac remodeling control therapy (RCT), drug therapy, cell therapy, and gene therapy. In various embodiments, implantable medical device 110 delivers the inspiratory muscle stimulation in conjunction with delivery of one or more other cardiac and/or respiratory therapies.

Lead 112A is an implantable transvenous lead that includes a proximal end 114A, a distal end 116A, and an elongate body 118A between proximal end 114A and distal end 116A. Proximal end 114A is configured to be connected to implantable medical device 110. One or more electrodes are incorporated into distal end 116A and/or the distal portion of elongate body 118A near distal end 116A for delivering the stimulation. In the illustrated embodiment, lead 112A is configured to allow placement of distal end 116A in left pericardiophrenic vein 104A such that the stimulation is delivered to left phrenic nerve 106A through the one or more electrodes. Lead 112A is configured to allow distal end 116A to advance to left pericardiophrenic vein 104A through left subclavian vein 102A.

Lead 112B is an implantable transvenous lead that includes a proximal end 114B, a distal end 116B, and an elongate body 118B between proximal end 114B and distal end 116B. Proximal end 114B is configured to be connected to implantable medical device 110. One or more electrodes are incorporated into distal end 116B and/or the distal portion of elongate body 118B near distal end 116B for delivering stimulation. In the illustrated embodiment, lead 112B is configured to allow placement of distal end 116B in right pericardiophrenic vein 104B such that the stimulation is delivered to right phrenic nerve 106B through the one or more electrodes. Lead 112B is configured to allow distal end 116B to advance to right pericardiophrenic vein 104B through left subclavian vein 102A and then right subclavian vein 102B.

In the illustrated embodiment, implantable medical device 110 is implanted in the left subclavicle area, and leads 112A-B both enter left subclavian vein 102A. In another embodiment, implantable medical device 110 is implanted in the left subclavicle area, and leads 112A-B both enter left subclavian vein 102A. In various embodiments, distal ends 116A-B are advanced to left and right pericardiophrenic vein 104A-B through any one or more viable veins including, but not limited to, one or more of left and right subclavian veins 102A-B and left and right internal jugular veins 103A-B.

External system 120 communicates with implantable medical device 110 and provides for access to implantable medical device 110 by a physician or other caregiver. In one embodiment, external system 120 includes a programmer. In another embodiment, external system 120 is a patient management system including an external device communicating with implantable medical device 110 via telemetry link 122, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 122 is an inductive telemetry link. In another embodiment, telemetry link 122 is a far-field radio-frequency (RF) telemetry link. Telemetry link 122 provides for data transmission from implantable medical device 110 to external system 120. This includes, for example, transmitting real-time physiological data acquired by implantable medical device 110, extracting physiological data acquired by and stored in implantable medical device 110, extracting patient history data such as occurrences of various pathological events and therapy deliveries recorded in implantable medical device 110, and/or extracting data indicating an operational status of implantable medical device 110 (e.g., battery status and lead impedance). Telemetry link 122 also provides for data transmission from external system 120 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies. In one embodiment, external system 120 receives a command from a physician or other caregiver or a patient to initiate a delivery of the inspiratory muscle stimulation.

Figure 2:
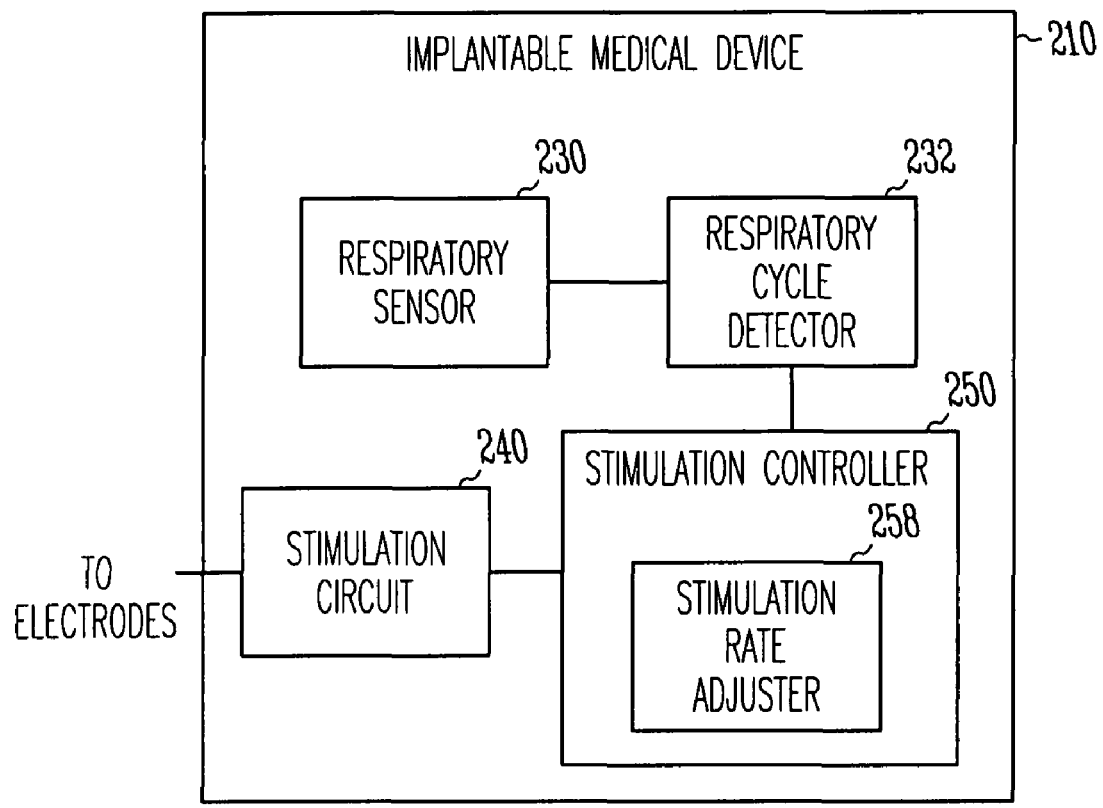
FIG. 2 is a block diagram illustrating an embodiment of an implantable medical device of the inspiratory muscle stimulation system.

FIG. 2 is a block diagram illustrating an embodiment of an implantable medical device 210, which represents an embodiment of implantable medical device 110. Implantable medical device 210 includes a respiratory sensor 230, a respiratory cycle detector 232, a stimulation circuit 240, and a stimulation controller 250. Respiratory sensor 230 senses one or more respiratory signals indicative of respiratory cycles and/or respiratory performance. Each respiratory cycle corresponds to a diaphragmatic contraction and has an inspiration phase and an expiration phase. Respiratory cycle detector 232 detects events indicative of the respiratory cycles using a respiratory signal indicative of respiratory cycles. The events indicative of the respiratory cycles include events that are detectable from the respiratory signal and occur at the respiratory rate, such as onsets and peaks of the inspiration phase and the expiration phase of each respiratory cycle. In one embodiment, respiratory cycle detector 232 calculates the respiratory rate using the detected events indicative of the respiratory cycles. In one embodiment, respiratory cycle detector 232 calculates an intrinsic respiratory rate using the events indicative of the respiratory cycles detected when no artificial stimulation is applied. The intrinsic respiratory rate is the frequency of respiration that occurs naturally (without artificial stimulation). Stimulation circuit 240 delivers the stimulation through electrodes. In one embodiment, the electrodes include the one or more electrodes incorporated into each of leads 112A-B. In various other embodiments, the electrodes include electrodes placed on or near left and right phrenic nerves 106A-B and/or diaphragm 108 to deliver the stimulation to left and right phrenic nerves 106A-B and/or diaphragm 108. Stimulation controller 250 controls the delivery of the stimulation using a stimulation rate and includes a stimulation rate adjuster 258. Stimulation rate adjuster 258 causes the stimulation to be delivered at a stimulation rate that is approximately equal to the intrinsic respiratory rate when the delivery of the stimulation is initiated. The respiratory cycles are adapted to the stimulation rate when the intrinsic respiratory cycles and the stimulation resonate during the delivery of the stimulation. In one embodiment, stimulation rate adjuster 258 causes the stimulation to be delivered in response to each detection of the events indicative of respiratory cycles such that the stimulation is synchronized to the intrinsic respiratory cycles to allow the intrinsic respiratory cycles and the stimulation to resonate. This allows the stimulation to gain control of the timing of the diaphragmatic contractions from the patient's intrinsic respiratory rhythm. Stimulation rate adjuster 258 then decreases the stimulation rate at a rate allowing the respiratory cycles to adapt to the stimulation rate until the stimulation rate reaches a specified target respiratory rate.

Figure 3:
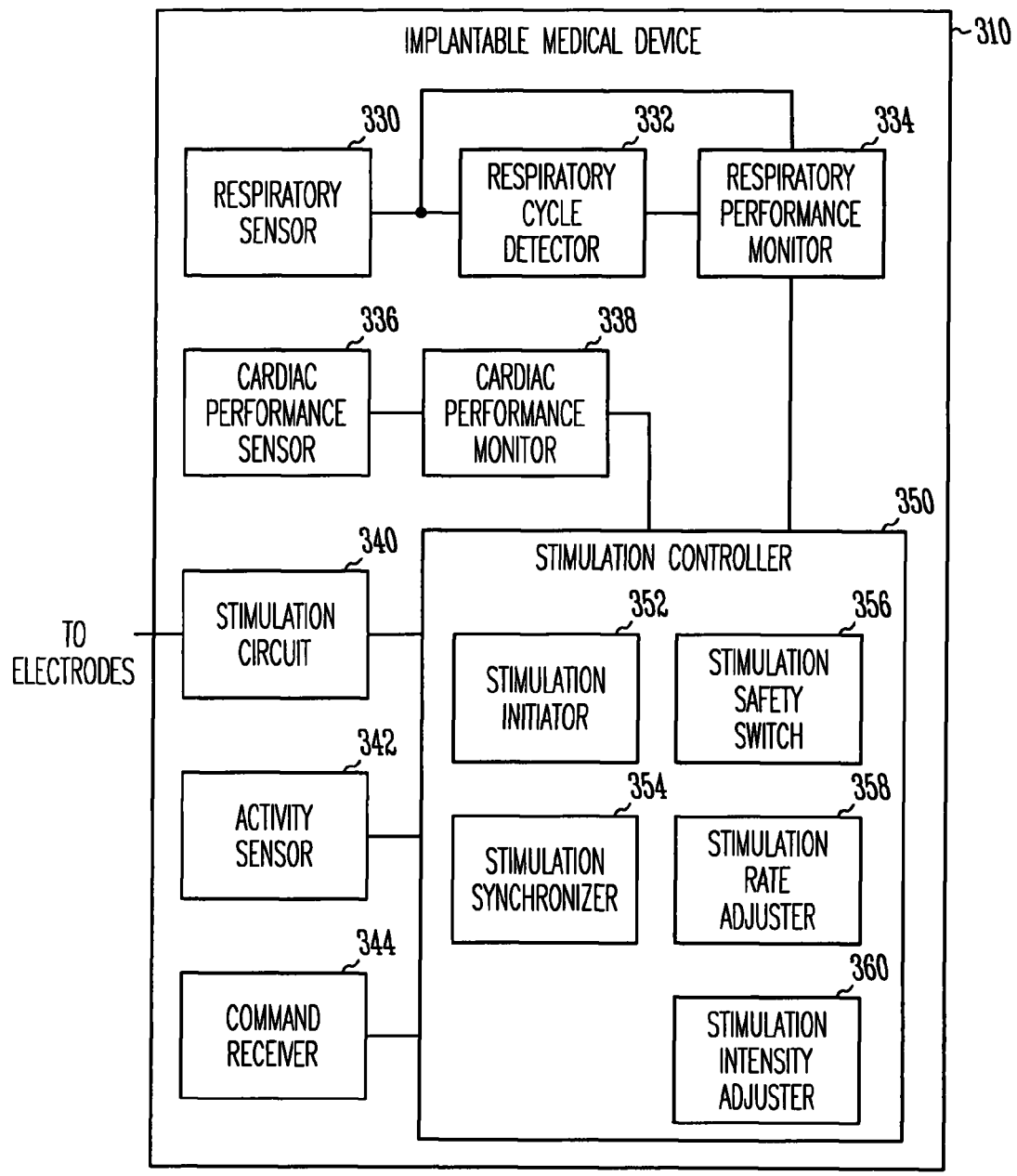
FIG. 3 is a block diagram illustrating another embodiment of the implantable medical device.

FIG. 3 is a block diagram illustrating an embodiment of an implantable medical device 310, which represents a specific embodiment of implantable medical device 210. Implantable medical device 310 includes a respiratory sensor 330, a respiratory cycle detector 332, a respiratory performance monitor 334, a cardiac performance sensor 336, a cardiac performance monitor 338, a stimulation circuit 340, an activity sensor 342, a command receiver 344, and a stimulation controller 350.

Respiratory sensor 330 represents a specific embodiment of respiratory sensor 230 and senses the one or more respiratory signals. In various embodiments, respiratory sensor 330 senses diaphragmatic movements or a physiologic parameter that varies as a result of the diaphragmatic movements. Examples of respiratory sensor 330 include one or more of an endovascular impedance sensor, an extravascular accelerometer, an endovascular strain-gauge sensor, an extravascular strain-gauge sensor, an intracardiac pressure sensor, a photoplethysmographic sensor, and an endobronchial flow sensor.

Respiratory cycle detector 332 represents a specific embodiment of respiratory cycle detector 232 and detects the events indicative of respiratory cycles. In one embodiment, respiratory cycle detector 332 detects the intrinsic respiratory rate as an average of intrinsic respiratory rates associated with a specified number of respiratory cycles.

Respiratory performance monitor 334 detects one or more respiratory performance parameters indicative of respiratory performance from the one or more respiratory signals and/or one or more other sensed physiological signals. Examples of the respiratory performance parameters include tidal volume, minute ventilation, and a blood carbon dioxide level. The tidal volume is the volume of gas expired per breath. A higher tidal volume indicates a "deeper" breath. The minute ventilation is the total exhaled volume in liters per minute. Because the minute ventilation is the product of the tidal volume and the respiratory rate, its value can be maintained by increasing the tidal volume while decreasing the respiratory rate (i.e., deeper, slower breathing). The blood carbon dioxide level is a carbon dioxide level in arterial blood. An abnormally high blood carbon dioxide level indicates hypoventilation. In one embodiment, the events indicative of respiratory cycles and the one or more respiratory performance parameters are detected using the same respiratory signal. In another embodiment, the events indicative of respiratory cycles and the one or more respiratory performance parameters are detected using two or more respiratory signals.

Cardiac performance sensor 336 senses a signal indicative of cardiac performance. In one embodiment, the signal is indicative of cardiac output. In another embodiment, the signal is indicative of cardiac preload. Examples of the signal indicative of cardiac performance includes electrocardiogram, intracardiac electrogram, hemodynamic signal indicative of hemodynamic performance, pressure signal, photoplethysmogram, and impedance signal.

Cardiac performance monitor 338 detects one or more cardiac performance parameters each being a measure of the cardiac performance from the signal indicative of cardiac performance. In one embodiment, the one or more cardiac performance parameters include the cardiac output. In various embodiments, cardiac performance monitor 338 detects cardiac events indicative of a need for respiratory stimulation. Examples of such cardiac events includes tachyarrhythmia such as ventricular fibrillation, sudden decrease of intrinsic heart rate, changes in myocardial contraction dynamics preceding syncope, irregular or minimal cardiac output, and poor hemodynamic performance.

Stimulation circuit 340 represents a specific embodiment of stimulation circuit 240 and delivers the stimulation through the electrodes. In one embodiment, the stimulation is delivered bilaterally to left and right phrenic nerves 106A-B for balanced diaphragmatic contractions. In another embodiment, the stimulation is delivered to diaphragm 108 directly.

Stimulation controller 350 represents a specific embodiment of stimulation controller 250 and includes a stimulation initiator 352, a stimulation synchronizer 354, a stimulation safety switch 356, a stimulation rate adjuster 358, and a stimulation intensity adjuster 360. In one embodiment, stimulation controller 350 controls the delivery of the stimulation using stimulation parameters including a stimulation rate (or stimulation interval) and a stimulation duration. The stimulation duration is a time interval during which the stimulation is delivered at the stimulation rate. In one embodiment, the stimulation is delivered on an approximately periodical basis using a specified stimulation period. In one embodiment, the stimulation includes electrical pulses delivered in bursts. Stimulation controller 350 controls delivery of bursts of electrical pulses using additional stimulation parameters including burst duration (or number of pulses per burst, pulse frequency (or inter-pulse interval), pulse amplitude, and pulse width. The stimulation parameters are further discussed below, with reference to FIGS. 4 and 5. In various embodiments, stimulation controller 350 includes a microprocessor or other processing circuit programmed to execute one or more inspiratory muscle stimulation algorithms each controlling the delivery of the stimulation using stimulation parameters such as those described in this document. Examples of such algorithms include an inspiratory muscle training algorithm for inspiratory muscle training that enhances respiratory capacity by conditioning and strengthening the inspiratory muscle, a respiratory performance algorithm for respiratory performance improvement by treating various breathing disorders, a cardiac performance algorithm for cardiac performance improvement by regulating hemodynamic functions such as blood pressure, blood return, and cardiac output, and an autonomic balance algorithm for regulating autonomic balance by controlling sympathetic and parasympathetic tones.

Stimulation initiator 352 initiates the stimulation duration during which the stimulation is delivered at the stimulation rate. In one embodiment, the stimulation is applied for inspiratory muscle training. Stimulation initiator 352 initiates the stimulation duration at specified delivery times according to a stimulation schedule, such as on the approximately periodical basis using the stimulation period. In various embodiments, stimulation initiator 352 ensures that the stimulation duration is initiated when the patient's physical activity is at a minimal level. For example, the specified delivery times include times when the patient is expected to be sleeping or have minimal physical activity. In a specific embodiment, activity sensor 342 senses a signal indicative of a physical activity level of the patient. Stimulation initiator 352 initiates the stimulation duration when the activity level is below a specified threshold level during a specified delivery time. In another embodiment, the stimulation is applied for improving respiratory performance. Stimulation initiator 352 initiates the stimulation duration using the one or more respiratory performance parameters, such as when one or more respiratory performance parameters indicate a poor respiratory performance, such as when the intrinsic respiratory rate falls below a specified threshold rate, when the minute ventilation falls below a specified minimum minute ventilation, when Cheyne-Stokes Respiration is detected, or when the carbon dioxide level rises above a specified threshold. In another embodiment, the stimulation is applied for improving cardiac performance. Stimulation initiator 352 initiates the stimulation duration using the one or more cardiac performance parameters, such as when the one or more cardiac performance parameters indicate a cardiac output that is below a threshold cardiac output, when the blood pressure rises above a threshold blood pressure, or when the cardiac preload rises above a threshold preload. In another embodiment, the stimulation is applied for regulating sympathetic and parasympathetic tones. Stimulation initiator 352 initiates the stimulation duration using one or more cardiac performance parameter or other signals indicative of autonomic balance. In one embodiment, command receiver 344 receives a command from a physician or other caregiver or the patient. Stimulation initiator 352 initiates the stimulation duration in response to the user command. This allows, for example, the patient to initiate the delivery of the stimulation when he or she feels an impending syncope prior to a sensor response. In various embodiments, stimulation initiator 352 initiates the stimulation duration using one or more of the specified delivery times, respiratory rate and other respiratory performance parameter(s), activity level, cardiac performance parameter(s), and user command.

Stimulation synchronizer 354 synchronizes the delivery of the stimulation to the respiratory cycles. In one embodiment, stimulation synchronizer 354 detects an onset of the inspiration phase of each of the respiratory cycles and triggers the delivery of each of the bursts of electrical pulses in response to the detection of the onset of the inspiration phase.

Stimulation safety switch 356 inhibits the delivery of the stimulation using the one or more respiratory performance parameters. The inhibition of the delivery of the stimulation includes stopping the delivery of the stimulation or disallowing the initiation of the delivery of the stimulation. In one embodiment, stimulation safety switch 356 inhibits the stimulation when the one or more respiratory performance parameters indicate hypoventilation or hyperventilation. When the one or more respiratory performance parameters indicate hypoventilation, stimulation safety switch 356 allows or inhibits the delivery of the stimulation, depending on whether the stimulation has been delivered. When hypoventilation in indicated while the stimulation is not being delivered, stimulation safety switch 356 allows (i.e., does not inhibit) initiation of delivery of the stimulation. When hypoventilation is indicated while the stimulation is being delivered, stimulation safety switch 356 stops the delivery of the stimulation because the stimulation may have contributed to the hypoventilation or is at least ineffective. Thus, in various embodiments, stimulation safety switch 356 inhibits the delivery of the stimulation when the minute ventilation is below a specified minimum minute ventilation, when the minute ventilation exceeds a specified maximum minute ventilation, and/or when the carbon dioxide level falls outside a specified normal range defined by one or more threshold carbon dioxide levels. In various embodiments, stimulation safety switch 356 also inhibits the delivery of the stimulation when one or more substantial changes in the patient's physical, physiologic, and pathophysiologic conditions are detected. For example, stimulation safety switch 356 inhibits the delivery of the stimulation in response to detection of substantial change in activity level, posture, or heart rate.

Stimulation rate adjuster 358 represents a specific embodiment of stimulation rate adjuster 258 and causes the stimulation to be delivered at a stimulation rate that is approximately equal to the intrinsic respiratory rate when the delivery of the stimulation is initiated. In one embodiment, stimulation rate adjuster 358 causes the stimulation to be delivered in response to each detection of the events indicative of respiratory cycles such that the stimulation is synchronized. After the respiratory cycles are under the control of the stimulation, such as after a specified period of time, stimulation rate adjuster 258 decreases the stimulation rate at a rate allowing the respiratory cycles to adapt to the stimulation rate until a target respiratory rate is reached. The inspiratory muscle is then trained by diaphragmatic contractions stimulated at the target respiratory rate, which is lower than the detected intrinsic respiratory rate.

Stimulation intensity adjuster 360 adjusts one or more of stimulation intensity parameters using the one or more cardiac performance parameters. In one embodiment in which the stimulation uses the bursts of electrical pulses, the stimulation intensity parameters include the burst duration (or number of pulses per burst, pulse frequency (or pulse period or inter-pulse interval), pulse amplitude, and pulse width. In one embodiment, stimulation intensity adjuster 360 adjusts at least one of the stimulation intensity parameters to increase the intensity of the stimulation (and hence the depth of breathing) when the cardiac output is below a specified threshold cardiac output. In another embodiment, stimulation intensity adjuster 360 adjusts at least one of the stimulation intensity parameters using the one or more respiratory performance parameters. In a specific embodiment, stimulation intensity adjuster 360 adjusts at least one of the stimulation intensity parameters to increase intensity of the stimulation (and hence the depth of breathing) when the tidal volume is below a specified minimum tidal volume. In another specific embodiment, stimulation intensity adjuster 360 adjusts at least one of the stimulation intensity parameters to increase intensity of the stimulation (and hence the depth of breathing) when the minute ventilation is below a specified minimum minute ventilation, and to decrease intensity of the stimulation (depth of breathing) when the minute ventilation exceeds a specified maximum minute ventilation. In another specific embodiment, while stimulation intensity adjuster 360 adjusts at least one of the stimulation intensity parameters, stimulation rate adjuster 358 increases the stimulation rate when the minute ventilation is below a specified minimum minute ventilation, and decreases the stimulation rate when the minute ventilation exceeds a specified maximum minute ventilation. In one embodiment, the maximum minute ventilation is specified to a value below a previous average minute ventilation to prevent hyperventilation. In various embodiments, stimulation intensity adjuster 360 adjusts at least one of the stimulation intensity parameters using the one or more respiratory performance parameters and the one or more cardiac performance parameters. In various embodiments, stimulation rate adjuster 358 and/or stimulation intensity adjuster 360 maintains the minute ventilation at a substantially constant value by adjusting one or more of the stimulation rate and the stimulation intensity parameters.

FIG. 4 is a timing diagram illustrating an embodiment of stimulation parameters for inspiratory muscle stimulation. In the illustrated embodiment, the stimulation parameters are used to control delivery of bursts of electrical pulses on an approximately periodic basis. FIG. 4 shows a respiratory signal 400 and the bursts of electrical pulses. Each delivery of the stimulation includes delivery of N bursts of electrical pulses. A stimulation interval 402 is time interval between to bursts of electrical pulses and corresponds to the stimulation rate at which the bursts of electrical pulses are delivered. The stimulation rate depends on the patient's intrinsic respiratory rate. A stimulation duration 404 is the duration of one delivery of the stimulation during which the bursts of electrical pulses are delivered at the stimulation rate. In one embodiment, the stimulation duration is between 15 minutes to 60 minutes. A stimulation period 406 is the period at which stimulation duration 402 is initiated. In one embodiment, the stimulation period is between 24 and 96 hours. In one embodiment, the periodic stimulation as illustrated in FIG. 4 is applied for inspiratory muscle training. A physician or other caregiver determines an inspiratory muscle training schedule that specifies the number of training sessions each has the stimulation duration. The training is completed when that number has been reached, unless restarted by the physician or other caregiver.

FIG. 5 is an illustration of an embodiment of a burst of electrical pulses for inspiratory muscle stimulation. The illustrated burst of electrical pulses includes M pulses. A pulse period 510 (inverse of pulse frequency) is the period at which pulses 1-M are delivered. A burst duration 512 is a time interval during which pulses 1-M are delivered and can alternatively be specified by the number of pulses (M) in the burst. A pulse amplitude 514 is the voltage or current amplitude of the electrical pulses. A pulse width 516 is the width of each of pulses 1-M.

Figure 6:
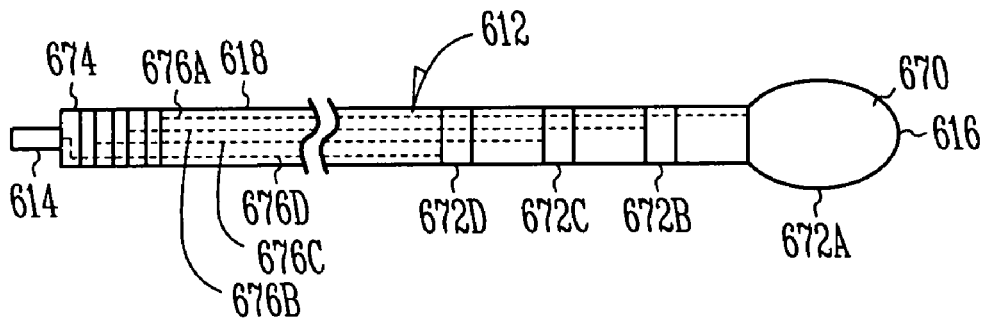
FIG. 6 is an illustration of an embodiment of an implantable transvenous lead for delivering stimulation to a phrenic nerve.

FIG. 6 is an illustration of an embodiment of an implantable transvenous lead 612 for delivering stimulation to a phrenic nerve. Lead 612 represents an embodiment of each of leads 112A-B.

Lead 612 has a proximal end 614, a distal end 616, and an elongate body 618 between proximal end 614 and distal end 616. In the illustrated embodiment, stimulation electrodes 672A-D are distributed on distal end 616 and a distal portion of elongate body 618. In various embodiments, one or more stimulation electrodes are distributed on one or more of distal end 616 and elongate body 618 to deliver the stimulation. A connector 674 at proximal end 614 provides for electrical and mechanical connection between lead 612 and implantable medical device 110. Conductors 676A-D are each connected between one of stimulation electrodes 672A-D and connector 674.

Distal end 616 includes a gravity fixation device 670 that has a weight suitable for substantially stabilizing the distal end in a vein such as one of left and right pericardiophrenic veins 104A-B. In the illustrated embodiment, stimulation electrode 672A is incorporated onto, or forms, gravity fixation device 670. Thus, gravity fixation device 670 includes stimulation electrode 672A.

Lead 612 is configured to allow distal end 616 and a distal portion of elongate body 618 to be placed in one of left and right pericardiophrenic veins 104A-B. For lead placement, distal end 616 is advanced one of left and right pericardiophrenic veins 104A-B through one or more of left and right subclavian veins 102A-B and/or through one of left and right internal jugular veins 103A-B. Advantage of delivering the stimulation by transvenous access, such as using lead 612, include avoidance of permanent damage to phrenic nerves 106A-B, minimal invasiveness, low risk of infection, short hospital stay, and similarity to the implantation technique used to implant a cardiac pacing lead.

The detailed structures and materials for lead 612 are similar to the structures and materials used in implantable cardiac pacing leads such as discussed in U.S. Pat. No. 6,141,594, "SINGLE PASS LEAD AND SYSTEM WITH ACTIVE AND PASSIVE FIXATION ELEMENTS," U.S. Pat. No. 6,463,334, "EXTENDABLE END RETRACTABLE LEAD," U.S. Pat. No. 6,915,169, "EXTENDABLE AND RETRACTABLE LEAD HAVING A SNAP-FIT TERMINAL CONNECTOR," all assigned to Cardiac Pacemakers, Inc., which are incorporated herein by reference in their entirety. In one embodiment, lead 612 is made by adopting and/or modifying structures and elements of such an implantable cardiac pacing lead to include the novel features discussed in this document with reference to FIGS. 6-9.

To implant an implantable transvenous lead such as lead 612 for phrenic nerve stimulation, a guiding catheter is introduced into a subclavian vein or an internal jugular vein through an introducer and then canulate a pericardiophrenic vein. A venogram may be required to create a road map for the lead placement. In one embodiment, a guide wire is introduced into the guiding catheter. The lead is advanced over the guide wire to the pericardiophrenic vein using the guiding catheter as a conduit. In another embodiment, the lead is delivered via a stylet using the guiding catheter as a direct delivery conduit. For bilateral stimulation, two leads are used, and both leads can be implanted through the same subclavian vein or jugular vein with one or more specifically shaped guiding catheter. The lead is connected to an implantable medical device such as implantable medical device 110. During the lead placement, the diaphragmatic movement in response to a test stimulation is monitored to optimize the lead location and to avoid cardiac stimulation.

In another embodiment, a lead is implanted by a minimally invasive laproscopic surgery. In another embodiment, stimulation electrodes are incorporated into devices implanted into pericardiophrenic veins 104A-B. These devices wirelessly communicate with an implantable medical device such as implantable medical device 110, or an external system such as external system 120.

Figure 7:
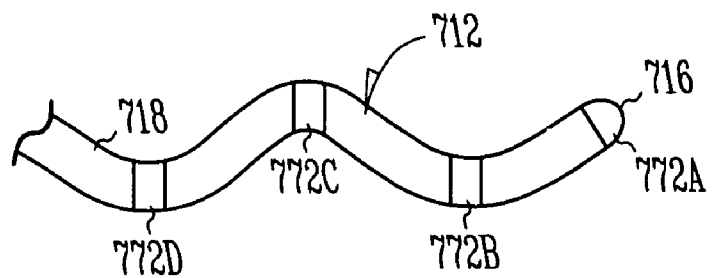
FIG. 7 is an illustration of another embodiment of an implantable transvenous lead for delivering stimulation to a phrenic nerve.

FIG. 7 is an illustration of an embodiment of a distal end 716 of an implantable transvenous lead 712 for delivering stimulation to a phrenic nerve. Lead 712 represents another embodiment of each of leads 112A-B. Lead 712 is substantially similar to lead 612 except that a distal portion of its elongate body 718 is biased for stabilizing distal end 716 in a vein such as one of left and right pericardiophrenic veins 104A-B. Electrodes 772A-D are distributed along the biased portion of elongate body 718. In one embodiment, gravity fixation device 670 is incorporated into distal end 716 to further stabilizing distal end 716 in the vein. In various embodiments, the implantable transvenous leads discussed in this document each include one or more fixation mechanism including, but not limited to, one or more of the gravity fixation devices or biased lead body as discussed in this document.

Figure 8:
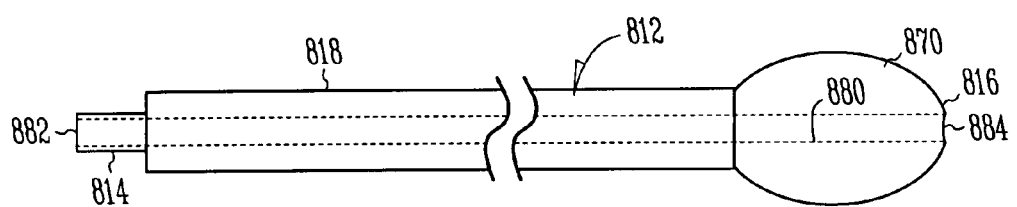
FIG. 8 is an illustration of another embodiment of an implantable transvenous lead for delivering stimulation to a phrenic nerve.

FIG. 8 is an illustration of an embodiment of an implantable transvenous lead 812 for delivering stimulation to a phrenic nerve. Lead 812 represents an embodiment of each of leads 112A-B and includes stimulation electrodes coupled to a connector via conductors in a way similar to lead 612.

As illustrated in FIG. 8, lead 812 has a proximal end 814, a distal end 816, and an elongate body 818 between proximal end 814 and the distal end 816. Distal end 816 includes a gravity fixation device 870 having a weight suitable for substantially stabilizing the distal end in a vein such as one of left and right pericardiophrenic veins 104A-B. A lumen 880 has a proximal opening 882 at proximal end 814 and a distal opening 884 at distal end 816. Lumen 880 extends with elongate body 818 and includes a portion as a tunnel within gravity fixation device 870. Lumen 880 is suitable for accommodating a portion of a guide wire used for implanting lead 812.

Figure 9:
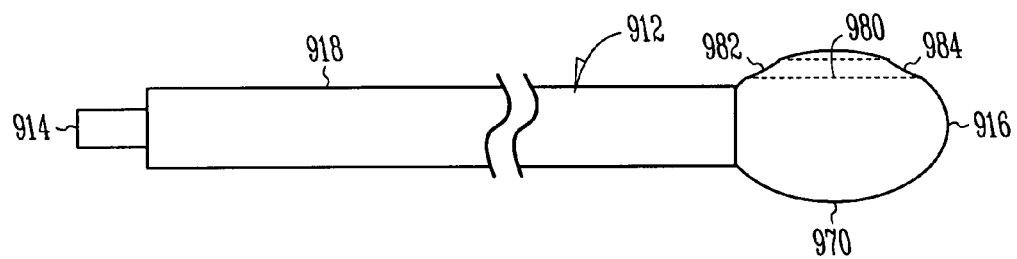
FIG. 9 is an illustration of another embodiment of an implantable transvenous lead for delivering stimulation to a phrenic nerve.

FIG. 9 is an illustration of another embodiment of an implantable transvenous lead 912 for delivering stimulation to a phrenic nerve. Lead 912 represents another embodiment of each of leads 112A-B and includes stimulation electrodes coupled to a connector via conductors in a way similar to lead 612.

As illustrated in FIG. 9, lead 912 has a proximal end 914, a distal end 916, and an elongate body 918 between proximal end 914 and the distal end 916. Distal end 916 includes a gravity fixation device 970 having a weight suitable for substantially stabilizing the distal end in a vein such as one of left and right pericardiophrenic veins 104A-B. Gravity fixation device 970 includes a tunnel 980 having a proximal opening 982 and a distal opening 984. Tunnel 980 is suitable for accommodating a portion of a guide wire used for implanting lead 912.

Figure 10:
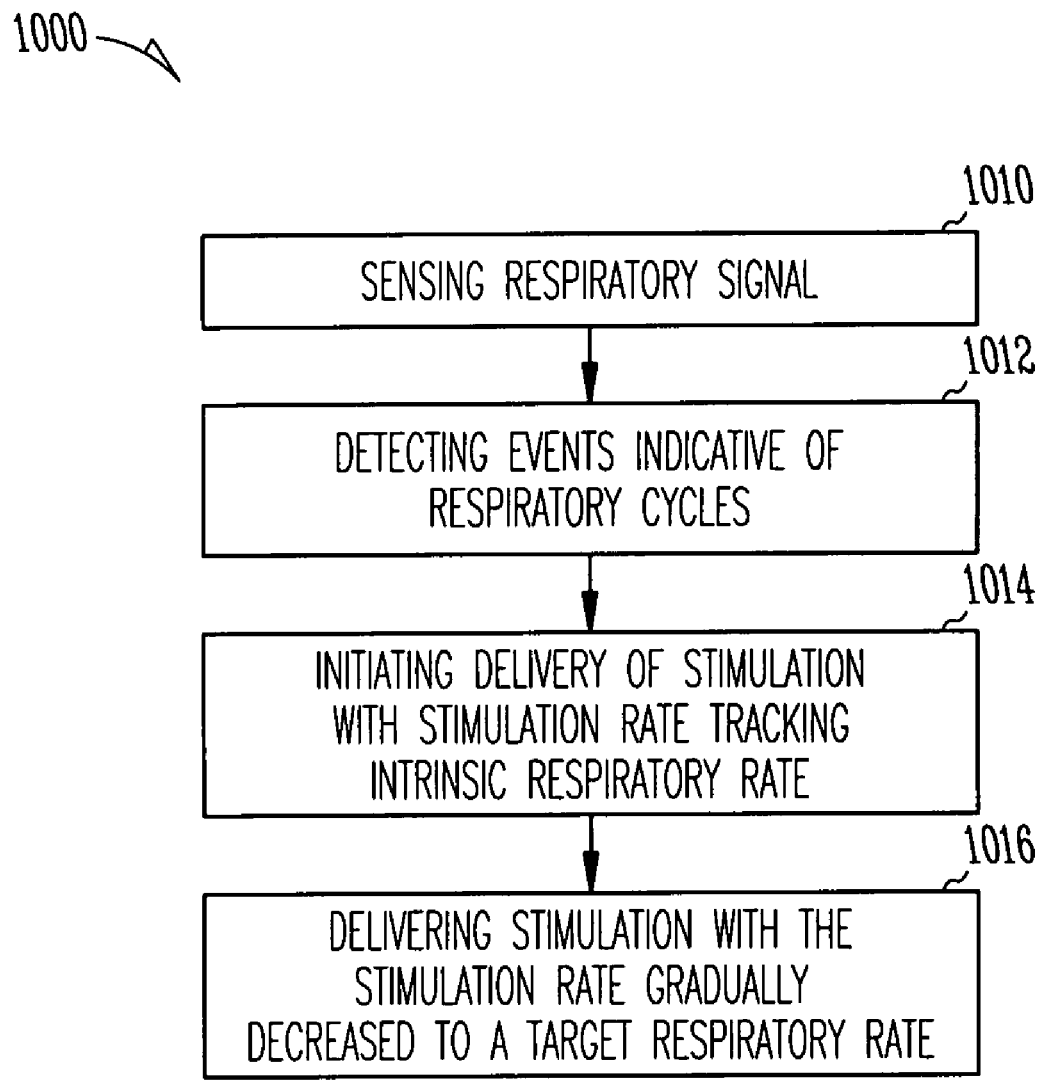
FIG. 10 is a flow chart illustrating an embodiment of a method for inspiratory muscle stimulation.

FIG. 10 is a flow chart illustrating an embodiment of a method 1000 for inspiratory muscle stimulation. In one embodiment, method 1000 is performed using implantable medical device 210. In various embodiments, method 1000 is applied for inspiratory muscle training, improving respiratory performance, improving cardiac performance, and regulating blood pressure and autonomic balance.

A respiratory signal indicative of respiratory activities and performance is sensed at 1010. Events indicative of respiratory cycles are detected using the respiratory signal at 1012. The events indicative of respiratory cycles include events that are detectable from the respiratory signal and occur at the respiratory rate. The respiratory rate is the intrinsic respiratory rate when artificial stimulation is not applied. In one embodiment, the respiratory rate is calculated using the detected events indicative of respiratory cycles. In a specific embodiment, the intrinsic respiratory rate is calculated using the events indicative of respiratory cycles detected when no inspiratory muscle stimulation is delivered. A delivery of stimulation is initiated at 1014. The stimulation is synchronized to the respiratory cycles and delivered by tracking the detected respiratory cycles such that the stimulation rate is approximately equal to the intrinsic respiratory rate. In one embodiment, the stimulation is delivered in response to each detection of the events indicative of respiratory cycles. The stimulation rate is decreased gradually at 1016, while the stimulation is being delivered, at a rate allowing the respiratory cycles to adapt to the stimulation rate. In one embodiment, the stimulation rate is decreased gradually at 1016 while the minute ventilation is maintained at a substantially constant value by adjusting the intensity of the stimulation (and hence the depth of breathing). In various embodiments, the stimulation is delivered to the phrenic nerves or the diaphragm of a patient to result in diaphragmatic contractions. By stimulating at the stimulation rate that approximately equals the detected intrinsic respiratory rate and then decreases gradually, the stimulation takes control of the diaphragmatic contractions from the patient's intrinsic respiratory rhythm. This forces the patient to have slower and deeper breath, thereby conditioning and strengthening the inspiratory muscles.

FIG. 11 is a flow chart illustrating another embodiment of a method 1100, which represents a specific embodiment of method 1000. In one embodiment, method 1100 is performed using implantable medical device 310.

A respiratory signal indicative of respiratory activities and performance is sensed at 1110. The respiratory signal is indicative of respiratory cycles. Each respiratory cycle has an inspiration phase and an expiration phase. Examples of the respiratory signal includes an endovascular impedance signal, an extravascular accelerometer signal, an endovascular or extravascular strain-gauge sensor signal, an intracardiac pressure sensor signal, a photoplethysmographic signal, a thoracic impedance signal, and an endobronchial flow signal. Such a respiratory signal includes components that result from either the diaphragmatic movements or physiological effects of the diaphragmatic movements. The events indicative of respiratory cycles are detected using the respiratory signal at 1112. In one embodiment, this includes detection of cyclic events such as onsets or peaks of the inspiratory phase or expiratory phase of the respiratory cycles. In one embodiment, the intrinsic respiratory rate is calculated using the events indicative of respiratory cycles detected when no inspiratory muscle stimulation is delivered.

Respiratory performance is monitored at 1114. In one embodiment, one or more respiratory performance parameters indicative of the respiratory performance are detected from the respiratory signal. Examples of such respiratory performance parameters include the tidal volume, minute ventilation, and blood carbon dioxide level. These respiratory performance parameters are indicative of abnormal events such as hypoventilation and hyperventilation.

Cardiac performance is monitored at 1116. A signal indicative of cardiac performance is sensed. Examples of such a signal includes electrocardiogram, intracardiac electrogram, blood pressure signal, photoplethysmogram, and transthoracic impedance signal. One or more cardiac performance parameters are detected from the signal indicative of cardiac performance. The one or more cardiac performance parameters are each a measure of the cardiac performance. In one embodiment, the one or more cardiac performance parameters includes cardiac output. In one embodiment, cardiac events indicative of a need for the inspiratory muscle training using the stimulation are detected. Examples of such cardiac events include tachyarrhythmia such as ventricular fibrillation, sudden decrease of intrinsic heart rate, changes in myocardial contraction dynamics preceding syncope, irregular or abnormally low cardiac output, high blood pressure, and other events indicative of poor hemodynamic performance.

Whether the stimulation is to be applied is determined at 1118. In various embodiments, depending on the purpose(s) of the stimulation, the delivery of the stimulation is to be triggered by one or more of a specified time according to a stimulation schedule, time of day, the intrinsic respiratory rate, physical activity level of the patient, an event or parameter indicative of poor respiratory performance (such as hypoventilation and Cheyne-Stokes Respiration), an event or parameter indicative of poor cardiac performance (such as low cardiac output, high blood pressure, and high cardiac preload), and a user command from a physician or other caregiver or the patient. In one embodiment, in which the stimulation is delivered for inspiratory muscle training, the delivery of the stimulation is triggered approximately periodically using a specified stimulation period and a signal indicative of the patient's physical activity level, such that the stimulation is delivered while the patient is at rest.

If the stimulation is to be applied as determined at 1118, a delivery of the stimulation is initiated by starting the stimulation duration at 1120, by allowing the stimulation rate to track the intrinsic respiratory rate. The stimulation is delivered bilaterally to the left and right phrenic nerves, or to the diaphragm. In one embodiment, the stimulation is delivered using two implantable transvenous lead such as one or more of leads 612, 712, 812, and 912 discussed above. Once initiated, the stimulation is delivered for a specified stimulation duration unless terminated due to safety reasons. In one embodiment, the stimulation includes delivery of bursts of electrical pulses. The stimulation parameter for controlling the delivery of the stimulation includes the stimulation period, the stimulation duration, and the stimulation rate, where the stimulation rate is the frequency at which the bursts of electrical pulses are delivered. In one embodiment, the intensity of the stimulation (and hence the depth of breathing) is controlled using stimulation intensity parameters including burst duration (or number of pulses per burst), pulse frequency (or inter-pulse interval), pulse amplitude and pulse width. These stimulation parameters are discussed above with reference to FIGS. 4 and 5. In one embodiment, the delivery of the bursts of electrical pulses is synchronized to the respiratory cycles. The onset of the inspiration phase of each respiratory cycle is detected from the respiratory signal, and a burst of electrical pulses is delivered in response to the detection of the onset of inspiration phase of each respiratory cycle.

The stimulation is delivered at 1122, with the stimulation rate gradually decreased to a target respiratory rate. The stimulation rate is decreased at a rate allowing the respiratory cycles to adapt to the stimulation rate. The target respiratory rate is lower than the intrinsic respiratory rate, thus forcing the patient to breathe more slowly. The depth of breathing is controlled by the stimulation intensity parameters. In one embodiment, while the stimulation is delivered, the minute ventilation is maintained at a substantially constant value by adjusting the intensity of the stimulation (and hence the depth of breathing).

If the delivery of the stimulation is completed at 1124, when the stimulation duration expires, the delivery of the stimulation is terminated at 1132. If the delivery of the stimulation is not completed at 1124, whether the stimulation is to be inhibited is determined at 1126. In various embodiments, the stimulation is inhibited for patient safety reasons, such as when a respiratory disorder is detected, and the stimulation may worsen the patient's respiratory and/or cardiac performance. Whether the stimulation is to be inhibited is determined using at least the one or more respiratory performance parameters. In various embodiments, the stimulation is inhibited when the minute ventilation is below a specified minimum minute ventilation, when the minute ventilation exceeds a specified maximum minute ventilation, and/or when the carbon dioxide level falls outside of a specified normal range defined by one or more threshold carbon dioxide levels. In one embodiment, whether the stimulation is to be inhibited is determined using the one or more respiratory performance parameters and the one or more cardiac performance parameters. If the stimulation is inhibited at 1126, the delivery of the stimulation is terminated at 1132.

If the stimulation is not inhibited at 1126, whether the stimulation intensity is to be adjusted is determined at 1128. In one embodiment, one or more of the stimulation intensity parameters are adjusted using the one or more cardiac performance parameters. For example, the stimulation intensity is increased for deeper breathing to increase cardiac output of the patient. In one embodiment, one or more of the stimulation intensity parameters are adjusted to increase intensity of the stimulation (and hence the depth of breathing) when the cardiac output is below a specified threshold cardiac output. In one embodiment, one or more of the stimulation intensity parameters are adjusted using the one or more respiratory performance parameters. For example, the stimulation intensity is increased for deeper breathing to increase the tidal volume and/or the minute ventilation. In one embodiment, one or more of the stimulation intensity parameters are adjusted to increase intensity of the stimulation (and hence the depth of breathing) when the tidal volume is below a specified minimum tidal volume. In one embodiment, one or more of the stimulation intensity parameters are adjusted to increase intensity of the stimulation (and hence the depth of breathing) when the minute ventilation is below a specified minimum minute ventilation, and adjusted to decrease intensity of the stimulation (and hence the depth of breathing) when the minute ventilation exceeds a specified maximum minute ventilation. In one embodiment, in addition to adjusting the one or more of the stimulation intensity parameters, the stimulation rate is increased when the minute ventilation is below a specified minimum minute ventilation, and decreased when the minute ventilation exceeds a specified maximum minute ventilation. In one embodiment, the maximum minute ventilation is specified to a value that does not exceed a previous average minute ventilation to prevent hyperventilation. If the stimulation intensity is to be adjusted at 1128, the stimulation rate and/or the one or more of the stimulation intensity parameters are adjusted at 1130. In various embodiments, this includes adjustment of one or more of the stimulation rate, the burst duration, pulse frequency, pulse amplitude, and pulse width, including their equivalents.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for use in a body having left and right phrenic nerves and left and right pericardiophrenic veins, the system comprising:
    an implantable medical device including:
        a respiratory sensor configured to sense a respiratory signal;
        a respiratory cycle detector configured to detect events indicative of respiratory cycles using the respiratory signal, the respiratory cycles indicative of an intrinsic respiratory rate;
        a respiratory performance monitor configured to detect one or more respiratory performance parameters indicative of respiratory performance from the respiratory signal, the one or more respiratory performance parameters including a minute ventilation;
        a stimulation circuit configured to deliver stimulation; and
        a stimulation controller coupled to the respiratory cycle detector and the stimulation circuit, the stimulation controller programmed to control the delivery of the stimulation and including a stimulation rate adjuster programmed to cause the stimulation to be delivered at a stimulation rate that is approximately equal to the intrinsic respiratory rate for a period of time allowing the respiratory cycles to be under control of the stimulation and to decrease the stimulation rate after the period of time at a rate allowing the respiratory cycles to adapt to the stimulation rate until the stimulation rate reaches a specified target respiratory rate, the stimulation controller including a stimulation safety switch programmed to inhibit the delivery of the stimulation using the one or more respiratory performance parameters including the minute ventilation.

2. The system of claim 1, wherein the stimulation controller is programmed to execute an inspiratory muscle training algorithm adapted to control the delivery of the stimulation for inspiratory muscle training that enhances respiratory capacity.

3. The system of claim 1, wherein the stimulation controller is programmed to execute a respiratory performance algorithm adapted to control the delivery of the stimulation for respiratory performance improvement by treating various breathing disorders.

4. The system of claim 1, wherein the stimulation controller is programmed to execute a cardiac performance algorithm adapted to control the delivery of the stimulation for cardiac performance improvement by regulating hemodynamic functions.

5. The system of claim 1, wherein the stimulation controller is programmed to execute an autonomic balance algorithm adapted to control the delivery of the stimulation for regulating autonomic balance by controlling sympathetic and parasympathetic tones.

6. The system of claim 1, wherein the stimulation controller is programmed to control the delivery of stimulation using the stimulation rate and a stimulation duration during which the stimulation is delivered at the stimulation rate, and the stimulation controller comprises a stimulation initiator programmed to initiate the stimulation duration at a specified delivery time according to a stimulation schedule.

7. The system of claim 6, wherein the implantable medical device comprises an activity sensor configured to sense a signal indicative of an activity level, and the stimulation initiator is programmed to initiate the stimulation duration when the activity level is below a specified threshold level at the specified delivery time.

8. The system of claim 1, wherein the implantable medical device comprises a command receiver configured to receive a user command, and the stimulation controller comprises a stimulation initiator programmed to initiate a delivery of the stimulation in response to the user command.

9. The system of claim 1, wherein the implantable medical device comprises:
- a cardiac performance sensor configured to sense a signal indicative of cardiac performance; and
- a cardiac performance monitor configured to detect one or more cardiac performance parameters from the signal indicative of cardiac performance.

10. The system of claim 9, wherein the stimulation initiator is programmed to initiate the delivery of the stimulation when the one or more cardiac performance parameters indicate a need for delivering the stimulation.

11. The system of claim 9, wherein the stimulation controller is programmed to control the delivery of stimulation using the stimulation rate, the stimulation duration, and one or more stimulation intensity parameters controlling an intensity of the stimulation, and the stimulation controller comprises a stimulation intensity adjuster programmed to adjust the one or more of the stimulation intensity parameters using the one or more cardiac performance parameters.

12. The system of claim 1, wherein the stimulation initiator is programmed to initiate the delivery of the stimulation when the one or more respiratory performance parameters indicate a need for delivering the stimulation.

13. The system of claim 1, wherein the stimulation controller is programmed to control the delivery of stimulation using the stimulation rate, the stimulation duration, and one or more stimulation intensity parameters controlling an intensity of the stimulation, and the stimulation controller comprises a stimulation intensity adjuster programmed to adjust the one or more of the stimulation intensity parameters using the one or more respiratory performance parameters.

14. The system of claim 13, wherein the stimulation rate adjuster and the stimulation intensity adjuster are programmed to maintain the minute ventilation at a substantially constant value by adjusting the stimulation rate and the one or more of the stimulation intensity parameters.

15. The system of claim 1, comprising first and second implantable transvenous leads each including:
- a proximal end configured to be connected to the stimulation circuit;
- a distal end configured to be placed in one of the left and right pericardiophrenic veins;
- an elongate body between the proximal end and the distal end;
- one or more stimulation electrodes distributed on one or more of the distal end and the elongate body to deliver stimulation to one of the left and right phrenic nerves; and
- a gravity fixation device at the distal end, the gravity fixation device having a weight suitable for substantially stabilizing the distal end in the one of the left and right pericardiophrenic veins.

16. The system of claim 15, wherein the gravity fixation device of each of the first and second implantable transvenous leads comprises one of the one or more stimulation electrodes.

17. The system of claim 15, wherein the gravity fixation device of each of the first and second implantable transvenous leads comprises a tunnel configured to accommodate a portion of a guide wire.

18. The system of claim 17, wherein the first and second implantable transvenous leads each comprise a lumen extending within the elongate body and including the tunnel, the lumen configured to accommodate a portion of the guide wire and having a proximal opening at the proximal end and a distal opening at the distal end.

19. The system of claim 1, wherein the stimulation controller comprises a stimulation synchronizer programmed to synchronize the delivery of the stimulation to the respiratory cycles.

20. The system of claim 19, wherein the stimulation synchronizer is programmed to detect an onset of inspiration phase of each of the respiratory cycles and triggers delivery of a burst of electrical pulses in response to the detection of the onset of the inspiration phase.

21. The system of claim 1, wherein the stimulation safety switch is programmed to inhibit the delivery of the stimulation when the minute ventilation is below a specified minimum minute ventilation and when the minute ventilation exceeds a specified maximum minute ventilation.

* * * * *